United States Patent [19]

Kain

[11] 3,999,440

[45] Dec. 28, 1976

[54] FLEXIBLE PROBE AND STORAGE MEANS FOR A PORTABLE GAS DETECTOR

[75] Inventor: John F. Kain, Marblehead, Mass.

[73] Assignee: General Electric Company, Schenectady, N.Y.

[22] Filed: Oct. 24, 1975

[21] Appl. No.: 625,787

[52] U.S. Cl. .................................. 73/431; 55/270; 116/114 P
[51] Int. Cl.² .................. G01N 31/00; G01D 11/24
[58] Field of Search ...................... 73/431, 23, 19; 340/242; 324/33; 204/1 S, 1 T, 1 Y, 1 R; 55/270; 206/328, 329; 116/114 P

[56] References Cited

UNITED STATES PATENTS

| | | | |
|---|---|---|---|
| 1,676,673 | 7/1928 | Stalker | 73/431 |
| 1,888,288 | 11/1932 | Purdy et al. | 206/328 X |
| 2,033,491 | 3/1936 | Sprague et al. | 73/431 X |
| 2,290,328 | 7/1942 | Hedfield et al. | 73/431 X |
| 3,107,517 | 10/1963 | Loyd et al. | 73/431 X |
| 3,360,135 | 12/1967 | Horecki | 206/328 X |
| 3,559,049 | 1/1971 | Liebermann et al. | 340/242 X |

*Primary Examiner*—Richard C. Queisser
*Assistant Examiner*—Daniel M. Yasich
*Attorney, Agent, or Firm*—Vale P. Myles

[57] ABSTRACT

A manually portable gas detector instrument characterized by having an elongated flexible probe mounted thereon in association with a conveniently usable probe storage means that is operable to retain the probe within a circumferential channel around the instrument housing in a nested position such that the probe may be used to detect gas while thus stored.

11 Claims, 4 Drawing Figures

FLEXIBLE PROBE AND STORAGE MEANS FOR A PORTABLE GAS DETECTOR

BACKGROUND OF THE INVENTION

This invention relates to manually portable gas detecting instruments, and more particularly to a type of instrument having an elongated gas sensing probe mounted thereon to enable a gas sensing element to be moved into relatively inaccessible locations. More specifically, this invention is characterized by including means integral with the housing of such an instrument for storing a flexible probe mounted on it in a protected, nested relationship in which the probe can be readily operated to perform a gas sensing function.

Prior to the invention of the convenient gas detector instrument and associated probe storage means disclosed and claimed herein, the manufacture and use of various types of manually portable instruments having elongated flexible probes coupled thereto was generally well known. Such prior art devices can be broadly categorized into four groups for purposes of brief analysis. First, there are manually portable instruments that are designed to be housed in small cases provided with a handle for carrying the instrument. Ordinarily a coiled, extensible electric cord is plugged into such an instrument to couple it with a sensor assembly that can be extended from the carrying case when the probe is being used to detect a gas or other substance being monitored with the instrument. In such devices, the probe assembly and extensible flexible cord is normally stored within the carrying case when it is not in use, but the probe assembly is not conveniently useable to perform its sensing function when stored within the case. A common modification of the type of instruments within this first general grouping simply provides a hand held instrument with a flexible sensing probe permanently mounted thereon, but does not provide any means for storing the probe in a compact and conveniently portable position relative to the meter, in the manner provided by the present invention. An example of such a prior art meter and associated flexible probe assembly is shown in U.S. Pat. No. Des. 196,875, which issued on Nov. 12, 1963.

A second group or general class of prior art instruments having flexible probes mounted thereon is exemplified by the portable voltage tester illustrated in U.S. Pat. Des. No. 211,088, which issued on May 21, 1968. The voltage tester shown in that patent incorporates within its housing a probe retaining means that secures one probe in operating position on the end of the instrument housing. In association therewith is a second probe coupled to the housing with a resilient flexible electrical conductor. Instruments in this group are similar to those in the first group discussed above in that they do not provide a means for conveniently nesting the flexible portion of the extensible probe assembly in a protected, compact relationship with the instrument housing when the probe is stored. Moreover, as appears to be the case with the voltage tester illustrated in the aforesaid patent, such instruments frequently do not provide means for storing the flexibly mounted probe in a position such that it can be operated to enable the instrument to perform its indicating function while the probe is in its stored position.

A third grouping of such prior art instruments is characterized by providing a portable instrument housing having flexible probe storage means thereon that are operable to partially protect the probe when it is moved to its stored position. In such instruments the protective feature is normally accomplished by moving the probe into a recess or groove in the instrument housing when the probe is rotated to a stored position, in which it is no longer conveniently accessible to afford a sensing function. This third grouping of prior art instruments is, therefore, somewhat similar to a fourth grouping that typically provides a telescopically mounted probe on a portable instrument. This kind of probe is operable to be retracted within the instrument housing when the probe is not in use. Such a telescopically mounted probe on a portable gas detecting instrument is depicted, for example, in U.S. Pat. No. 3,559,049.

All of the aforementioned prior art types of manually portable instruments having flexible probe assemblies associated therewith have certain common disadvantages. Relative to the advantageous features of the present invention, the more outstanding of such disadvantages are that, heretofore, so far as the Applicant knows, none of these devices have provided an integral flexible probe storage means that is operable to retain a flexible sensing probe in a compact, protected relationship to an instrument housing, while at the same time enabling the probe to be conveniently used to perform a sensing function. Moreover, such prior art instrument and probe assemblies typically have not combined a flexible probe function with a hand-held instrument in a manner such that the probe assembly can be compactly stored to enable the instrument to be conveniently fitted into an operator's pocket when not in use.

SUMMARY OF THE INVENTION

In one preferred form of the invention a manually portable gas detector instrument is provided with a flexible probe mounted in operating relationship on the instrument housing, in combination with a probe storage channel and retaining means built into the instrument housing to enable the flexible probe to be compactly nested in a stored position wherein it is wrapped around the circumference of the housing in a recessed channel in a manner that enables the instrument to be readily carried in an operator's pocket. A pair of resilient clamping jaws on the instrument housing are operable to retain the probe sensing head in an operating position when the probe is compactly nested in its stored position. Characteristically, the probe storage means is effective to store at least 90 percent of the length of the flexible probe in a compact relationship to the housing, and the storage means preferably includes a strain relief mounting for the probe that is effective to prevent damage to the instrument circuitry due to mechanical forces transmitted through the probe.

OBJECTS OF THE INVENTION

A primary object of the invention is to provide a manually portable gas detector instrument having an integral, flexible probe storage means that is effective to protectively nest at least 90 percent of a flexible probe in a stored position on the housing while simultaneously enabling the probe to perform a sensing function.

Another object of the invention is to provide a readily portable, hand held detector instrument that overcomes the above-mentioned disadvantages of related prior art instruments.

Yet another object of the invention is to provide a manually portable gas detector instrument having a flexible probe mounted thereon, with a probe strain relief means that prevents the probe from transmitting injurious shock to the interior circuitry of the instrument.

Additional objects and advantages of the invention will become apparent to those skilled in the art from the description of the invention presented herein, considered in connection with the associated drawings.

DESCRIPTION OF THE PREFERRED EMBODIMENT

Figure 1:
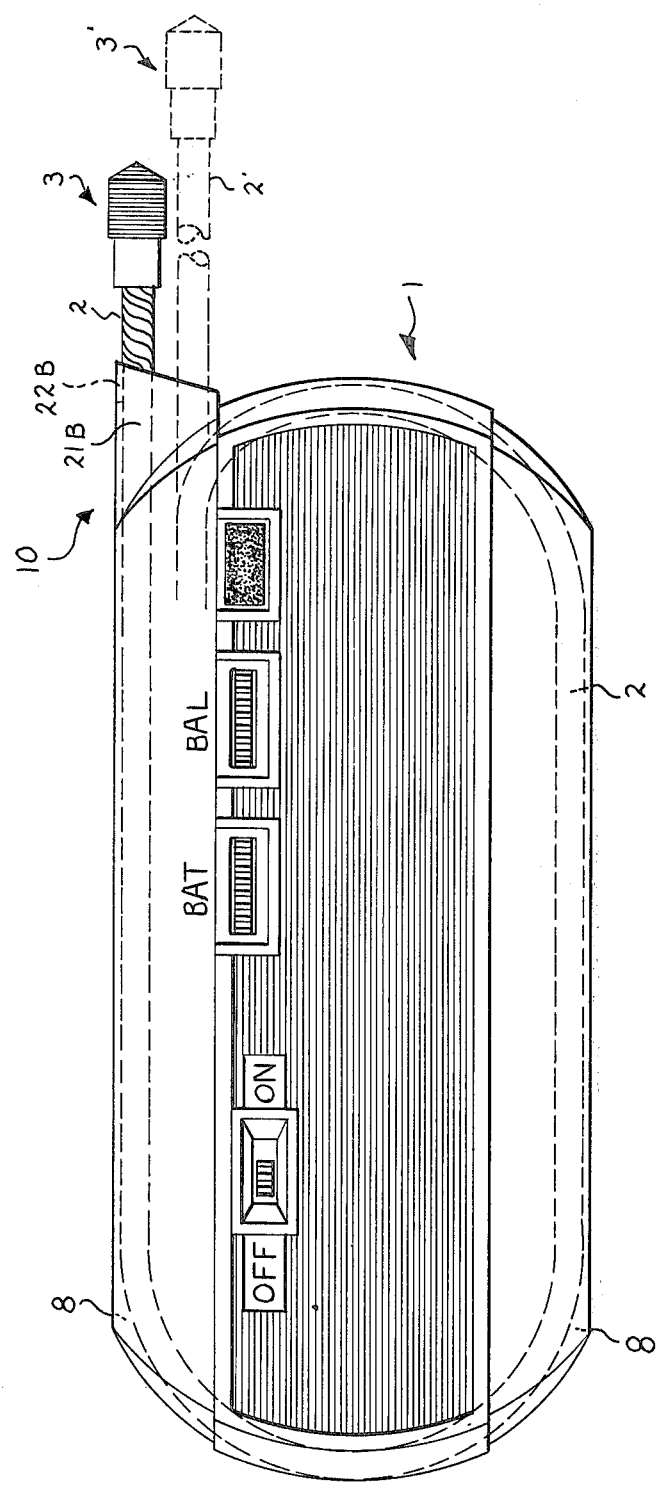
FIG. 1 is a side elevation view, partly in phantom, illustrating a manually portable gas detector instrument having an elongated flexible sensor probe mounted thereon and shown in both a stored position and, in phantom, in a partly extended position, all constructed in accordance with the teachings of the present invention.

Referring to FIG. 1 of the drawing, it will be seen that there is shown a manually portable gas detector instrument 1 that has an elongated flexible probe 2 mounted on it in a manner that will be described more fully below. The probe 2 has a gas detecting sensor assembly 3 supported thereon at the outer end of the probe. In this embodiment of the invention the housing of instrument 1 is formed of a commercially available, moldable, high impact plastic material, but it will be understood that other suitable instrument housing materials may be used in alternative embodiments of the invention. Basically, the housing of instrument 1 is molded in two separate parts, which are secured together by two retaining screws (not shown) that are slidably inserted through apertures in one of the parts and rotatably threaded into the other part, in any suitable well known manner. A hollow, relatively flexible steel tube of spirally wound conduit is used to form the flexible probe 2 in the preferred embodiment of the invention described herein; however, other conventional flexible materials may be used in practicing the invention, so long as they can be formed into given configurations that enable the probe assembly 3 to be moved into relatively inaccessible locations such as those often encountered in attempting to detect leaks in portable refrigerating systems mounted in confined areas, e.g., those encountered around the refrigerating systems of automobile air-conditioners.

Figure 2:
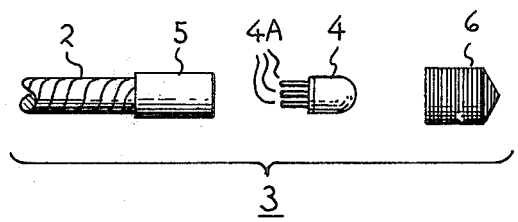
FIG. 2 is an exploded, fragmentary side elevation view of a gas sensor assembly such as that used on the outer end of the probe assembly illustrated in FIG. 1.

Before proceeding further with a description of the flexible probe storage means of the invention, reference is now made to FIG. 2 of the drawing to provide a fuller understanding of the constituent parts of sensor assembly 3. Although this particular sensor assembly does not form an essential part of the present invention, except insofar as it provides a sensor for the instrument 1, it should be understood that the assembly 3 comprises a commercially available plug-in type gas sensor 4 which is sealed in plastic to prevent its contamination. The sensor 4 has its three electrical terminals 4a plugged into a connector socket assembly 5 that has 3 terminals (not shown) connected, respectively, to wires that extend through the flexible probe 2 into associated electrical instrument circuitry housed in the instrument 1. This connection will be described more fully below. In order to prevent plugging of the sensor 4 by dirt or grease when it is moved into contact with such materials during normal operation, the sensor 4 is covered with a conventional spiral-spring protector 6 that is mounted over the socket assembly 5 by being twisted onto it. Of course, other types of sensor assemblies might be employed in alternative embodiments, or a "sniffer" nozzle might be mounted on the outer end of the flexible probe 2 in instruments that provide suitable sensor mechanisms mounted within the housing of an associated instrument, such as within instrument housing 1 illustrated herein.

As described thus far, the component parts of the embodiment of the invention shown in FIG. 1 are relatively conventional. The improvements of the present invention incorporated in the instrument 1 comprise a unique wall means 7A, 7B and 7C (best seen in FIGS. 3 and 4) which comprise the respective sides (7A, 7C) and the bottom (7B) that define a probe-receiving, generally U-shaped channel in an outer surface of the instrument housing 1. Actually the channel is U-shaped in cross-section only where molded struts extend between the surfaces 7A, 7C and the surface 7B, but is sufficiently so to restrict lateral movement of probe 2 in the channel. The probe-receiving channel 8 defines a nearly closed loop around the housing of instrument 1.

In the preferred form of the invention the channel 8 has a desired relationship to the dimensions of the flexible probe 2 such that the probe is relatively snuggly nested within the narrows of channel 8 thus being wound around the casing, as shown in FIG. 1, so that at least 90 percent of the probe length is retained in the channel when the probe 2 is in its stored position, as will be described more fully below. In particular, in this form of the invention the probe 2 is formed of a flexible steel tube that has a substantially constant outer diameter that preferably does not exceed one-quarter of an inch so that the probe can be inserted into relatively confined spaces while at the same time being rigid enough to retain sheet configurations. Accordingly, the mean width of the narrow portions of channel 8 between the edges of side walls 7A and 7C does not exceed three-sixteenths of an inch and the depth of the channel 8 from the upper lips of the sides 7A and 7C to the bottom wall means 7B does not exceed three-eighths of an inch, and all of these dimensions are greater than one-eighth of an inch. To provide a relatively uniform channel that secures the flexible probe in the desired manner, the width of the mouth of channel 8 is formed substantially constant and not more than 50 percent greater than the outer diameter of the probe 2 at any point along its length. With this relative arrangement of the component parts of the invention, the probe 2 can be compactly stored around the housing of instrument 1 in channel 8, as shown in FIG. 1.

There is also shown in FIG. 1, in phantom view, an extended arrangement of the probe 2. It will be understood that in the extended position the probe 2' is no longer housed in channel 8, but is unwound from channel 8 and protrudes outwardly (as shown in phantom) to any desired configuration such that the sensor 3' in this arrangement of the probe 2' can be positioned in any desired relationship with respect to instrument housing 1. Of course, the probe 2' and sensor assembly 3' are equivalent to the probe 2 and sensor 3 respectively, but are designated with a prime symbol in FIG. 1 to identify the alternative arrangement of the probe illustrated in phantom therein.

Figure 4:
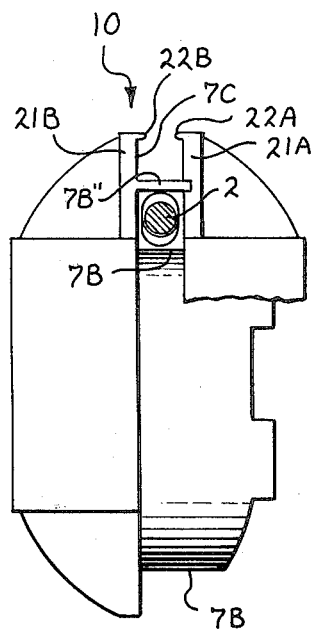
FIG. 4 is an end elevation view of the instrument and probe assembly illustrated in FIG. 3 including a portion of the other half of the housing, and showing the probe assembly in its stored position relative to the instrument housing.
Figure 3:
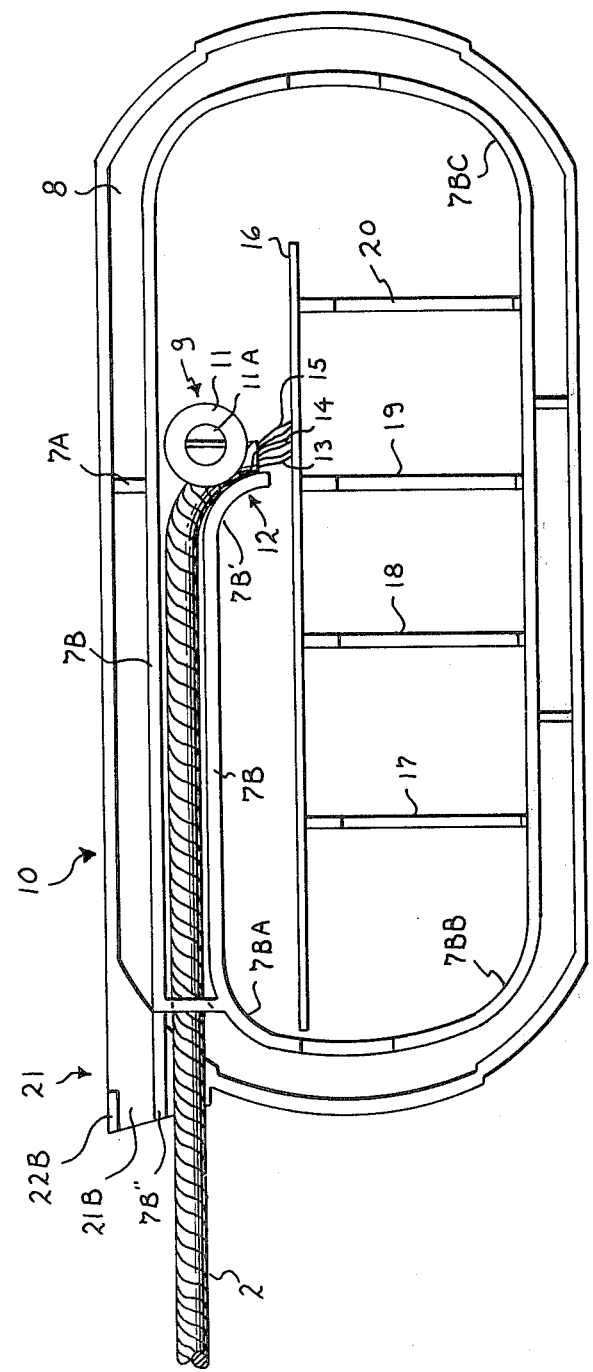
FIG. 3 is a side elevation view of an interior side of one-half of the instrument housing illustrated in FIG. 1, showing a flexible-probe storage channel arrangement and a probe strain relief means constructed according to the present invention.

Referring now to FIGS. 3 and 4, a probe mounting means 9 used in this embodiment of the invention for mounting one end of the probe 2 on the housing will be described, along with a description of the probe retaining means 10 that is constructed pursuant to the teaching of the invention for retaining the outer end of probe 2 in a predetermined position relative to the instrument housing 1 when the probe is positioned in its stored relationship in the channel 8. As best seen in FIG. 3, the mounting means 9 comprises a conventional metal washer 11 that is forced against the flexible probe 2 adjacent the inner end thereof by a conventional threaded screw 11A that is threaded into a suitable aperture molded or otherwise formed in the interior surface of instrument housing 1. Alternatively, a threaded sleeve or metal insert may be suitably secured in an aperture in the housing by shrink fitting or other manufacturing methods well known in the art to receive such a screw. Thus, the washer 11 and screw 11A constitute a probe clamp that is manually adjustable to apply a clamping force to the flexible probe 2 at a point intermediate the ends thereof, as best shown in FIG. 3.

The mounting means 9 further includes a probe strain relief means, generally designated by the numeral 12 in FIG. 3, which comprises the rigid probe clamp 11, 11A and a curved surface 7B' that extends from the rigid clamp means 11, 11A to a generally straight portion of the bottom surface 7B of the generally U-shaped channel 8. This arrangement of the mounting means 9 and probe clamp 11, 11A acts as a strain relief for the three electrical conductors 13, 14 and 15 that extend from the outer end of the flexible probe 2 where they are electrically connected with the terminals 4A on sensor 4 to the inner ends thereof where the conductors 13, 14 and 15 are electrically connected to a printed circuit on the circuit board 16, which is mounted in any suitable, conventional manner within the instrument housing 1. In this embodiment of the invention the circuit board 16 is arranged to rest on vertical struts 17, 18, 19 and 20 as well as cooperating with similar struts (not shown) molded in the other half of the instrument housing 1. It will be understood that various conventional detector circuitry may be mounted on the circuit board 16, but to simplify the description of the present invention, such circuitry will not be described in detail herein because it does not relate directly to the essence of the present invention.

The probe retaining means of the invention generally identified by the numeral 10 comprises a resilient clip 21 that is operable to retain the probe 2 in position within the channel 8 without applying a continuous resilient pressure on it. In this form of the invention the clip 21 includes a pair of resilient jaws 21A and 21B (see FIGS. 1, 3 and 4). That are mounted adjacent opposite sides of the channel 8, and the clip further includes a pair of abutments 22A and 22B mounted, respectively, on the jaws 21A and 21B, as best see in FIG. 4. The abutments 22A and 22B are designed to be operable to force the jaws 21A and 21B away from one another in response to the probe 2 being forced between the abutments. The abutments 22A and 22B are also effective to engage the probe 2 and releasably retain it within the channel 8 after the probe has moved past the abutments into the channel. This novel configuration of the clip 21 and the abutments 22A and 22B serves to retain the probe 2 in operating relationship while it is compactly nested in stored position wherein it is wrapped in channel 8 around the instrument housing 1. As best seen in FIG. 1, in such a stored position the operator can grasp the instrument housing 1, by simply placing his hand around it and the nested probe 2 to move the sensor assembly 3 to search for gas leaks being monitored with the instrument 1.

In the preferred embodiment of the invention the jaws 21A and 21B of the probe retaining clip 21 are molded integrally with the respective parts or sides of the instrument housing 1 and extend outward therefrom in a direction generally tangential to the channel 8 adjacent thereto, as best seen in FIG. 3. Likewise, the abutments 22A and 22B are preferably formed adjacent the outermost edges of the respective jaws 21A and 21B, relative to the instrument housing 1. Thus, it will be seen that the jaws 21A and 21B in this form of the invention are integral with, and essentially define, one end of the channel 8 while the outer portion of the other end of channel 8 terminates adjacent the wall means defining the outer base surface 7B'' of the jaws 21A and 21B.

A final basic feature of the invention to be described relates to the optimum overall configuration of the probe-receiving channel 8 that is used with the preferred embodiment of invention disclosed herein. As seen in FIGS. 1 and 3, the instrument housing 1 in this form of the invention is oblong and generally rectangular in shape and the channel 8 extends around substantially all of the sides thereof except for the small area occupied by the base portion 7B'' of the jaws 21A and 21B. The bottom wall 7B of the channel 8 is formed to define predetermined radii of curvatures as shown at 7BA, 7BB, 7BC and 7BD. Each of these radii terminates substantially tangentially with planes parallel to, and radially inward from, the respective intersecting sides of the rectangular outline of the instrument housing 1. In addition, one of the radii of curvature on the bottom surface 7B of channel 8 constitutes the curved probe strain relief surface 7B' formed in the housing adjacent to the clamped end of the probe 2.

As most clearly seen in FIGS. 3 and 4, the bottom wall 7B of the U-shaped channel 8 is formed by a wide, continuous shelf in the form of a molded abutment projecting from the inner surface of on side of the molded instrument housing 1 past the center line thereof into the hollow half of the other side of the instrument housing 1. Thus, any radial inward movement of the flexible probe 1 is arrested by the bottom surface 7B defined by this shelf element. It will be appreciated that other suitable structures may be used for defining the base surface of the probe-receiving channel 8, but the illustrated preferred embodiment of the invention has been found to be particularly advantageous both from the standpoint of economy and structural strength of the resistant instrument and probe storing means of the invention.

Those skilled in the art will also understand that various modifications and improvements may be made in the invention without departing from the true scope of the invention in the following claims.

What I claim as new and desire to secure by Letters Patent of the United States is:

1. In a manually portable gas detector instrument having an elongated flexible probe with a gas detecting sensor supported thereon, the improvement comprising wall means defining a probe-receiving, generally U-shaped channel in an outer surface of said housing, mounting means for securely mounting one end of said probe on the housing, probe retaining means co-operating with said channel for retaining the other end of said probe in a predetermined position relative to the housing, said channel being formed to receive in nested relationship therein at least 90 percent of the length of said other end of said probe, a resilient portion of said probe retaining means being operable to releasably retain the other end of said probe in a relatively fixed position within said channel when the probe is positioned in said retaining means.

2. An invention as defined in claim 1 wherein said channel defines a nearly closed loop around said housing.

3. An invention as defined in claim 2 wherein said probe is formed of a flexible tube that has a substantially constant outer diameter, and wherein the width of said channel is substantially constant and not more than 50 percent greater than said outer diameter of the probe.

4. An invention as defined in claim 3 wherein said outer diameter does not exceed one quarter of an inch, the mean width of said channel does not exceed three-sixteenths of an inch, the depth of said channel does not exceed three-eighths of an inch, and all of said dimensions are greater than one-eighth inch.

5. An invention as defined in claim 1 wherein said mounting means includes probe strain relief means comprising a rigid probe clamp and a curved surface formed in said housing to define a probe supporting surface that extends from said rigid clamp to a bottom surface of said generally U-shaped channel, said probe clamp being manually adjustable to apply a clamping force to the probe at a point intermediate the ends thereof.

6. An invention as defined in claim 1 wherein said probe retaining means comprises a resilient clip that is operable to retain the probe in position without applying a continuous resilient pressure on it.

7. An invention as defined in claim 6 wherein said resilient clip comprises a pair of jaws mounted adjacent opposite sides of the channel, and a pair of abutments mounted, respectively, on said jaws, said abutments being operable to force the jaws away from one another responsive to the probe being forced between the abutments and being effective to engage the probe and releasably retain it within the channel after the probe has moved past the abutments into the channel.

8. An invention as defined in claim 7 wherein said jaws extend outward from the instrument housing in a direction tangential to said channel, said abutments being formed adjacent the outermost edges of said jaws, relative to said housing.

9. An invention as defined in claim 8 wherein said jaws are integral with one end of said channel and wherein the other end of said channel terminates adjacent wall means defining the outer base surface of said jaws.

10. An invention as defined in claim 9 wherein said housing is oblong and generally rectangular in shape and said channel extends around substantially all of the sides thereof except for the area occupied by the base of said jaws.

11. An invention as defined in claim 10 wherein the bottom wall of said channel defines predetermined radii of curvature that terminate substantially tangentially with planes parallel to the respective abutting sides of said generally rectangular shape, one of said radii comprising a curved probe strain relief surface formed in said housing adjacent the clamped end of the probe.

* * * * *